(12) United States Patent
DiSessa et al.

(10) Patent No.: US 12,011,386 B1
(45) Date of Patent: Jun. 18, 2024

(54) MAGNETIC ANTI-GRINDING DENTAL DEVICE, SYSTEM, AND METHOD

(71) Applicants: William G. DiSessa, Holly, MI (US); Mingma Tendu Sherpa, Kathmandu (NP)

(72) Inventors: William G. DiSessa, Holly, MI (US); Mingma Tendu Sherpa, Kathmandu (NP)

( * ) Notice: Subject to any disclaimer, the term of this patent is extended or adjusted under 35 U.S.C. 154(b) by 0 days.

(21) Appl. No.: 18/117,429

(22) Filed: Mar. 4, 2023

(51) Int. Cl.
*A61F 5/56* (2006.01)

(52) U.S. Cl.
CPC .......... *A61F 5/56* (2013.01); *A61F 2005/563* (2013.01)

(58) Field of Classification Search
CPC ...... A61F 5/56; A61F 5/566; A61F 2005/563; A61F 5/0006; A61F 5/0003; A61C 7/36; A61C 7/08; A61C 7/10; A61C 7/006; A63B 71/085; A63B 2071/086; A63B 2071/088; A61B 5/4557

See application file for complete search history.

(56) References Cited

U.S. PATENT DOCUMENTS

| | | | |
|---|---|---|---|
| 3,089,487 A | 5/1963 | Enicks et al. | |
| 3,984,915 A | 10/1976 | Noble et al. | |
| 4,253,828 A | 3/1981 | Coles et al. | |
| 4,396,373 A | 8/1983 | Dellinger | |
| 4,505,672 A | 3/1985 | Kurz | |
| 4,871,310 A | 10/1989 | Vardimon | |
| 5,103,838 A | 4/1992 | Yousif | |
| 10,173,015 B2 | 1/2019 | Fiedler et al. | |
| 10,470,847 B2 | 11/2019 | Shanjani et al. | |
| 10,888,201 B2 | 1/2021 | Pai | |
| 2006/0266356 A1 | 11/2006 | Sotos et al. | |
| 2022/0000585 A1 | 1/2022 | Cam et al. | |

*Primary Examiner* — Victoria Hicks Fisher
(74) *Attorney, Agent, or Firm* — Aundria Hairell

(57) ABSTRACT

Various disclosed embodiments relate to a dental appliance that includes a first lower tooth seat configured to accommodate at least one lower tooth and having a first lower magnet coupled thereto. The dental appliance also includes a second lower-tooth seat configured to accommodate at least one lower tooth and having a second lower magnet coupled thereto. Further, the dental appliance includes a support structure coupling the first lower-tooth seat to the second lower-tooth seat. Further still, the dental appliance includes a first upper-tooth seat configured to accommodate at least one upper tooth and having a first-upper magnet coupled thereto, the first upper-tooth seat movably coupled to the first lower-tooth seat. Yet further still, the dental appliance includes a second upper-tooth seat configured to accommodate at least one upper tooth and having a second-upper magnet coupled thereto, the second upper-tooth seat movably coupled to the second lower-tooth seat.

20 Claims, 17 Drawing Sheets

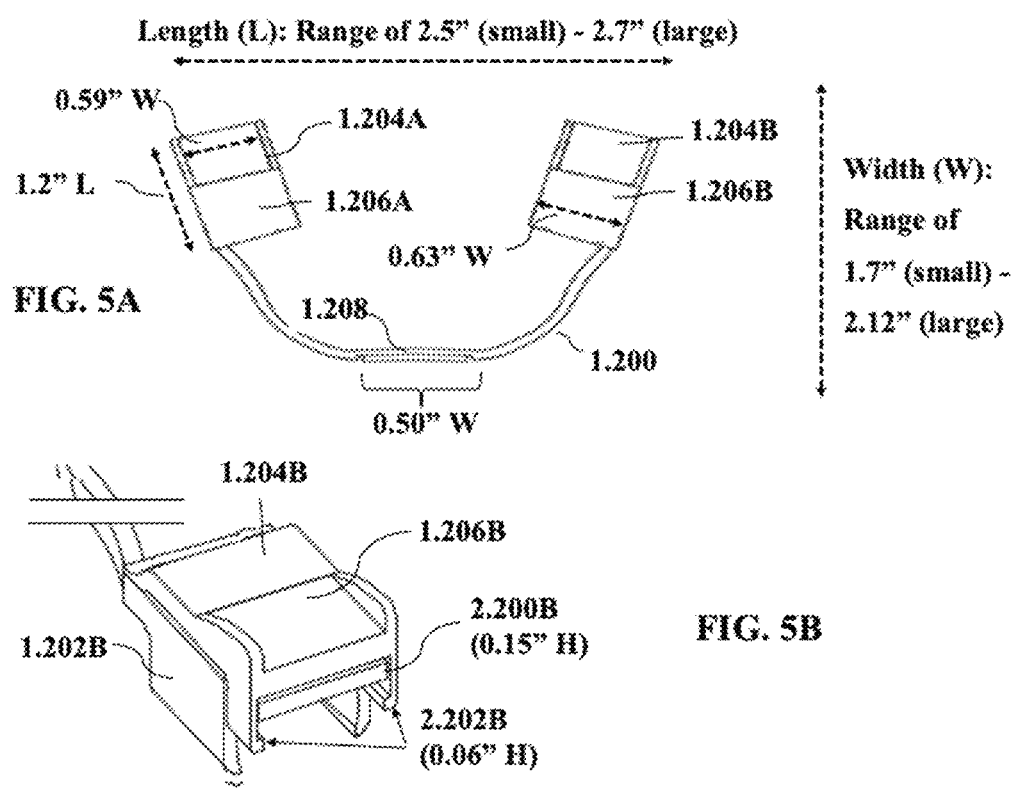

Prism-shaped buffer volume = 0.594 cubic in.

MAGNETIC ANTI-GRINDING DENTAL DEVICE, SYSTEM, AND METHOD

TECHNICAL FIELD

The present disclosure relates to devices, systems, and methods for aiding in users of the device to minimize grinding of teeth sometimes referred to as bruxism.

BACKGROUND

The statements in this section merely provide background information related to the present disclosure and may not constitute prior art.

Dental guards commonly are marketed as a solution to bruxism, a condition in which a person grinds, gnashes or clenches his or her teeth. Mouthguards are similar but typically designed for protection during contact sports.

Those with bruxism may unconsciously clench their teeth when awake (awake bruxism) or during sleep (sleep bruxism).

According to the Mayo Clinic, sleep bruxism is considered a sleep-related movement disorder (https://mayocl.in/2OYQMWi). People who clench or grind their teeth (brux) during sleep are more likely to have other sleep disorders, such as snoring and pauses in breathing (sleep apnea).

Though mild bruxism may not require treatment, in some people, bruxism can be frequent and severe enough to cause jaw disorders, headaches, damaged teeth, and other problems.

Normal chewing places 68 pounds-per-square-inch (PSI) of pressure on molars.

Deliberately clenching teeth causes 150 PSI of pressure. Unconscious grinding during sleep can be up to 900 PSI. Some people grind up to 40 minutes of every hour of sleep (https://bit.ly/2NU5VCB).

Several factors increase the risk of bruxism:
  Stress. Increased anxiety or stress can lead to teeth grinding. So can anger and frustration.
  Age. Bruxism is common in young children, but often goes away by adulthood.
  Personality type. Having a personality type that's aggressive, competitiveor hyperactive can increase one's risk of bruxism.
  Smoking tobacco, drinking caffeinated beverages or alcohol, or using recreational drugs may increase the risk of bruxism.
  Family members with bruxism. Sleep bruxism tends to occur in families. If you have bruxism, other members of your family also may have bruxism or a history of it.
  Other disorders. Bruxism can be associated with some mental health and medical disorders, such as Parkinson's disease, dementia, Gastroesophageal Reflux Disease (GERD), epilepsy, night terrors, sleep-related disorders such as sleep apnea, and Attention-Deficit/Hyperactivity Disorder (ADHD).

There are three main types of dental guards on the market to address bruxism:
  1. One-size-fits-all or various general sizes based on age or mouth size (e.g., small, medium or large);
  2. Boil-and-bite; and
  3. Custom-made.

The first two types are available via retail over the counter (OTC); the third typically is made by the patient's dentist from a full-mouth impression, and therefore is the most time-consuming and expensive.

Boil-and-bite models typically fit around all teeth (both arches have up to 18 teeth), and one-size-fits-all models, several molars and sometimes a premolar or two, depending on mouth size. Reusable and disposable options are available OTC.

Some models fit over the top or maxillary teeth, some fit over bottom or mandibular teeth, and the rest fit over both sets of teeth. The degree of fit varies from loose to tight, with custom-made models providing the tightest fit.

The problem: regardless of design, these dental guards all share similar shortcomings. They often:
  Impede a user's breathing and sleeping;
  Are dislodged or unconsciously expelled by the user; and
  Do little to solve the typically prolonged problem of bruxism, because users continue to grind their teeth or grind the dental guard itself—if it remains intact.

So, rather than reducing or eliminating bruxism, these devices cause additional problems without fully addressing the underlying condition itself. This is known as putting a figurative Band-aid on a problem's surface wound or symptoms, rather than addressing its underlying root cause and thereby preventing a recurrence of the problem.

SUMMARY

Disclosed embodiments include structures and methods for treating bruxism or teeth grinding.

An illustrative embodiment relates to a dental appliance. The dental appliance includes a first lower-tooth seat configured to accommodate at least one lower tooth and having a first-lower magnet coupled thereto. The dental appliance also includes a second lower-tooth seat configured to accommodate at least one lower tooth and having a second-lower magnet coupled thereto. Further, the dental appliance includes a support structure coupling the first lower-tooth seat to the second lower-tooth seat. Further still, the dental appliance includes a first upper-tooth seat configured to accommodate at least one upper tooth and having a first-upper magnet coupled thereto, the first-upper tooth seat movably coupled to the first lower-tooth seat. Yet further still, the dental appliance includes a second upper-tooth seat configured to accommodate at least one upper tooth and having a second upper magnet coupled thereto, the second upper-tooth seat movably coupled to the second lower-tooth seat.

Another illustrative embodiment relates to a dental appliance. The dental appliance includes a bite guard configured to resist teeth grinding. The dental appliance includes a structure configured to cause increasing repelling magnetic forces as surfaces of the bite guard come closer together. The dental appliance also includes a force-sensing circuit configured with the bite guard and configured to generate signals representative of bite force.

Another illustrative embodiment relates to a method. The method includes providing a dental appliance which resists teeth grinding by application of magnetic repulsion. The method also includes sensing the repulsive force. Further, the method includes sending a signal representative of the repulsive force to a computing device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Illustrative embodiments are illustrated in referenced figures of the drawings. It is intended that the embodiments and figures disclosed herein are to be considered illustrative rather than restrictive.

Like reference symbols in the various drawings generally indicate like elements.

DETAILED DESCRIPTION

Figure 1:
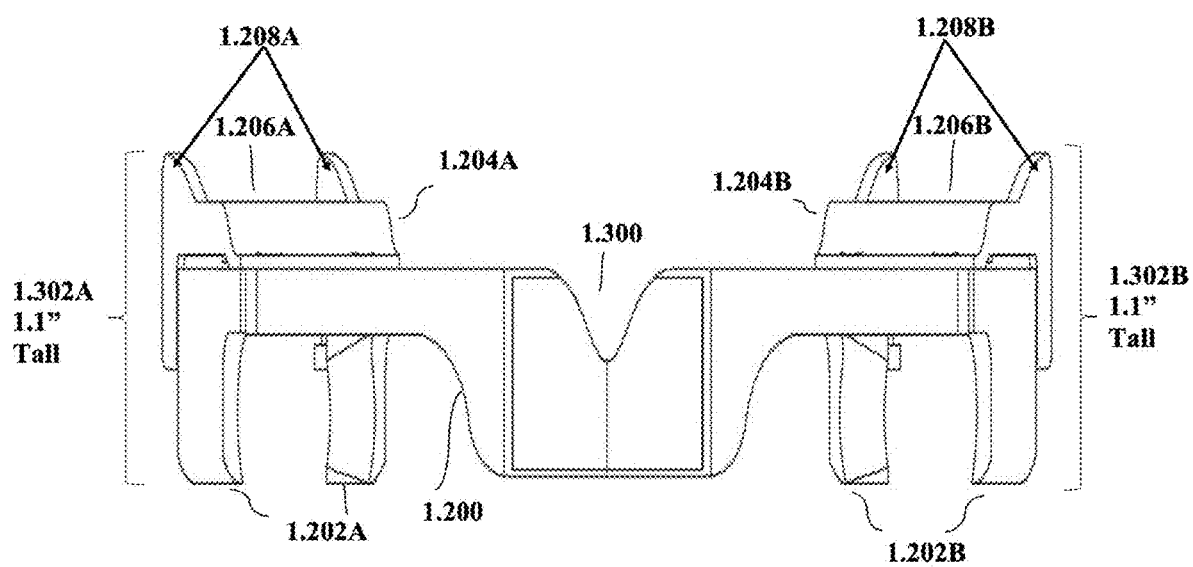
FIG. 1 is a front-view depiction of an exemplary embodiment of the dental guard (from the default point of view of looking from front to back of the device).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The disclosed subject matter is directed at solving the shortcomings of conventional dental guards through:

Unique deployment of repulsive or reverse magnetism, which creates a natural buffer between the upper and lower teeth, reduces bruxism during sleep, and may train the jaws over time to avoid teeth-grinding;

A streamlined, mostly single-layer design that still incorporates the two sets of opposing magnets necessary for the protective buffer; and A wireless tracking function so the user may adjust sleeping habits or current invention usage for even further improvements in comfort and performance.

The disclosed subject matter includes a support structure that may comprises a single strap or retention band, made of, for example but not limited to, clear or opaque acrylic plastic or similar material, which fits snugly over the bottom molars using a mostly single-layer fusion design to deploy a thin protective buffer between both sets of teeth. An array of opposing magnets generates this buffer.

The disclosed subject matter generates the reverse-magnetic buffer in a compact, streamlined design that avoids encasing all top and bottom teeth in two full layers of plastic, as in some retail models of dental guards.

The disclosed subject matter combines a design and algorithm for generating a protective magnetic buffer to strike an optimal balance between dental guard effectiveness and user comfort.

In at least one embodiment, an array of four opposing disc magnets, or eight in all, generates left- and right-side magnetic buffers, each approximately 2 centimeters (cm) or 0.7874 inch (in.) tall, between the upper and lower jaws.

The disclosed subject matter may include, in accordance with various embodiments and without limitation, a single piece of plastic, perhaps melded together from two or more pieces during an injection-molding process. So, all parts or design functions are interconnected without use of spring hinges, fasteners or exposed parts. Magnets and all other components are sealed within the plastic dental guard structure, so they remain free of moisture and there is no risk of them dislodging and being swallowed.

Figure 14:
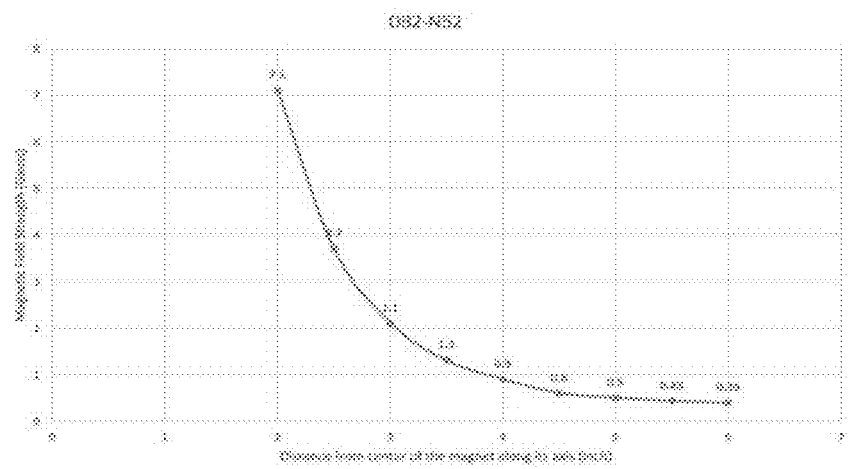
FIG. 14 is a chart showing the relationship between the distance along the D82-N52 magnet's Y-axis and its corresponding field strength.
Figure 15:
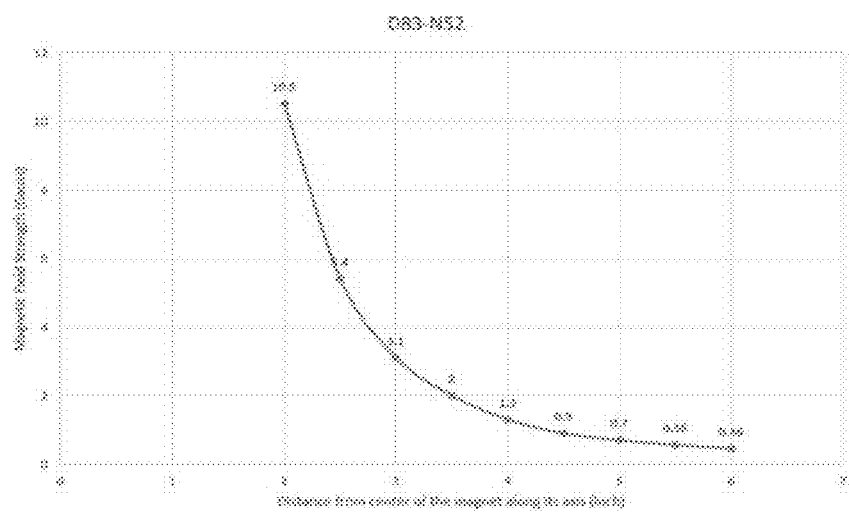
FIG. 15 is a chart showing the relationship between the distance along the D83-N52 magnet's Y-axis and its corresponding field strength.

The human mouth contains no magnetic dental components; so, there is no risk of interference with the disclosed subject matter (or vice versa) or risk to the user. Nor does there appear to be a risk to pacemakers as the maximum magnetic field in which a pacemaker may operate is 10 gauss—a level greater than the strength of the present invention's magnets. Specifically, using D82-N52 magnets as an example, the magnetic field at the surface of each magnet is 3,309 gauss, but field strength drops significantly with distance (https://bit.ly/3Q4qY73). Maximum field strength of the eight magnets falls to about 7.2 gauss, or 0.9 gauss per magnet, at a distance of 4 in. from center along the Y-axis (magnet's axis). For another magnet variety, D83-N52, the maximum field strength at the surface of each magnet is 4,440 gauss. But the maximum field strength of the eight magnets at 4.5 in. from the center also is 7.2 gauss or 0.9 gauss per magnet. Since the distance between the mouth and heart generally is greater than 4.5 in. along the torso, and the 10-gauss threshold is not exceeded under any condition, there is no conflict with conventional pacemakers. See FIGS. 14 and 15 for D82-N52 and D83-N52 magnets that show the relationship between the Each holster may contain:
Top teeth bite plates or placeholders that work in tandem with retention walls, which fit snugly over the bottom teeth, to keep the dental guard in place;

First and second holster walls anchoring the first and second upper- and lower-tooth seats and configured to keep the dental guard in place;

Upper and lower magnetic housings for generating the reverse-magnetic buffer; and Magnetic field sensor and microcontroller that track frequency of teeth-grinding, and wirelessly upload these data to a cloud server, where they are analyzed and sent to a smartphone app. Or alternatively, these data are sent directly to the smartphone app for processing and display, eliminating the need for the cloud server.

This exemplary embodiment of a dual-holster architecture provides a partial second level or overlay to accommodate top-teeth bite plates and upper-magnet housings without requiring two full levels covering all teeth. Contoured to fit comfortably in the human mouth, the holster's adaptive design follows top and bottom arch openings up to, e.g., 2 cm. A design safeguard then deploys, preventing the bite plates from opening beyond 2 cm while the jaws remain unimpeded. The safeguard may be, e.g., a hook-and-latch design that moves independently from its outer holster, and limits holster openings to 2 cm as a stopgap against wider jaw openings that may result in heavier teeth-grinding. This stopgap is designed to reduce, but not forcibly halt, jaw extensions beyond 2 cm.

Each holster's degree of closure depends on the bite force applied to its magnetic buffer, but full bite plate-on-plate closure likely is to recur assuming a heavy bite force is reapplied.

Referring now to FIG. 1, an exemplary embodiment of an arch-shaped dental guard is depicted having a plastic strap or retention band 1.200 connecting bifurcated left- and right-side seats or holsters for top and bottom teeth, specifically molars, as well as housings for associated components.

Anchoring the dental guard's left and right sides, for example, are 1.1-inch-tall holsters 1.302A/1.302B that together form the bite guard and its protection apparatus. They may be identical or mirrors of each other, each including: a hinged, partly two-layer structure 1.208A/1.208B that protects against teeth-grinding; and reverse-magnet housings on the hinged top 1.204A/1.204B and bottom layers 2.200A/2.200B, with the top layers doubling as bite plates 1.206A/1.206B for the top molars, and the bottom layers girded by bottom-molar retention walls 1.202A/1.202B to help keep the dental guard in place. The parallel retention walls may angle downward and inward about 5 degrees each, so both fit snugly over the bottom molars. In another exemplary embodiment, the retention walls' interiors are lined with, for example without limitation, ribbed, softer plastic or rubber to increase molar grip. The left- and right-side hinged top layers are designed to fit snugly under the top teeth, eliminating the need for their own retention walls or a containment strap.

The dental guard design broadly mimics an egg carton, celebrated for its simplicity, efficiency, and protectiveness. The exemplary embodiment's two holsters cradle upper and lower teeth, like eggs sitting in carton dimples, while the overall shell design, like the egg carton, allows for some natural give to account for movement of the arches during sleep.

The left side upper housing of magnets doubles as a foundation 1.204A for the upper teeth bite plate 1.206A. The right side housing of magnets doubles as a foundation 1.204B for the upper teeth bite plate 1.206B.

Fins 1.208A/1208B run alongside the left- and right-side upper bite plates to stabilize the top molars resting within. The bite plates are grooved to help keep the upper molars in place 4.208A/4.208B.

For user comfort, the retention band 1.200 provides an opening for the piece of soft tissue that runs in a thin line between the lips and gums. This opening is called a frenum or frenulum gap 1.300. By default, the frenum gap is located along the top of the front strap, but in other embodiments it could be located along the strap's bottom edge. As the frenum gap's strap location is a minor consideration, the user may reverse the dental guard without adversely impacting performance. In such a reversal, the frenum gap is on the strap bottom, with the bite plates laying over the bottom teeth, and the retention walls enclosing the top teeth. Other functions, such as the 2-cm safeguard or stopgap and deployment of magnetic buffers in each holster, are not impeded by the reversal.

Figure 2:
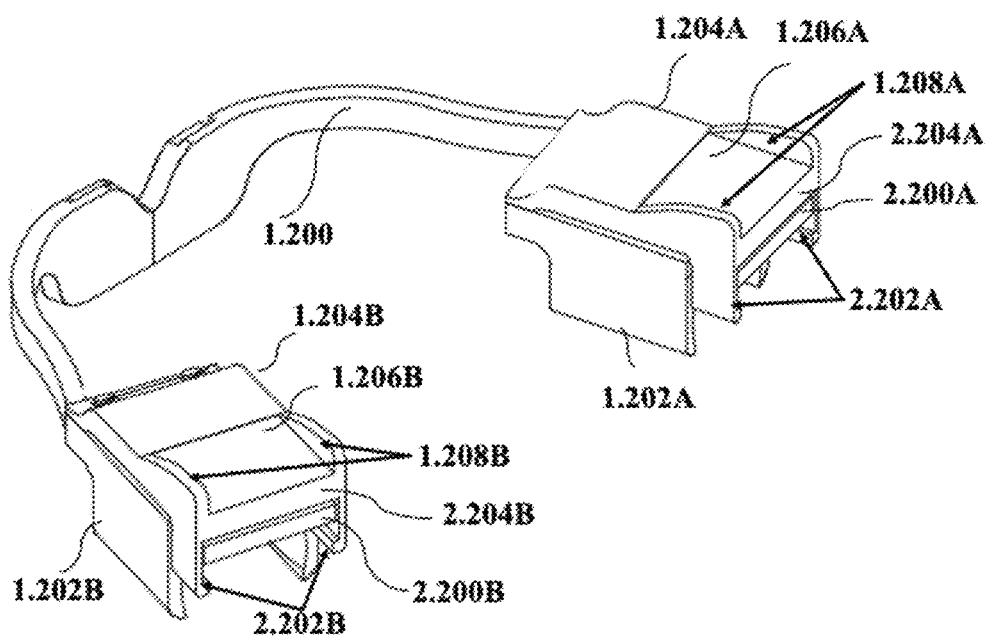
FIG. 2 is a top-angled-view depiction of the exemplary dental guard.

Referring now to FIG. 2, the lower left-2.200B and right-side 2.200A magnet housings serve as anchors or foundations for the dental guard holsters. The bite plates 1.206A/1.206B at the top of each side's holster and their hook-and-latch safeguards 2.202A/2.202B prevent or discourage jaw overextensions and corresponding heavy teeth-grinding. The hooks at the rear bottom edge of both holsters lock into place when the holsters, specifically their upper- and lower-magnet housings, fully extend, with the corresponding top and bottom arches, to 2 cm.

Figures 3A, 3B:
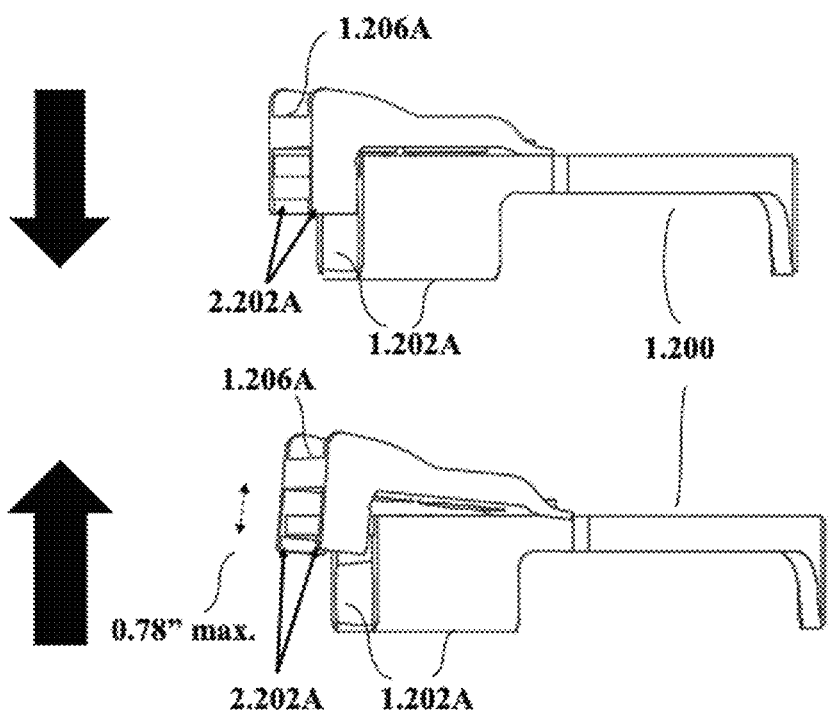
FIG. 3 (A and B) is a depiction of an exemplary embodiment of the dental guard's left side.

FIG. 3B shows the maximum 2-cm or 0.78-in. gap or chamber containing magnetic buffers between the left and right upper- and lower-magnet housings 1.302A/1.302B (see FIG. 1) for the top and bottom teeth, respectively. FIG. 3A shows upper and lower housings completely closed.

Figure 4:
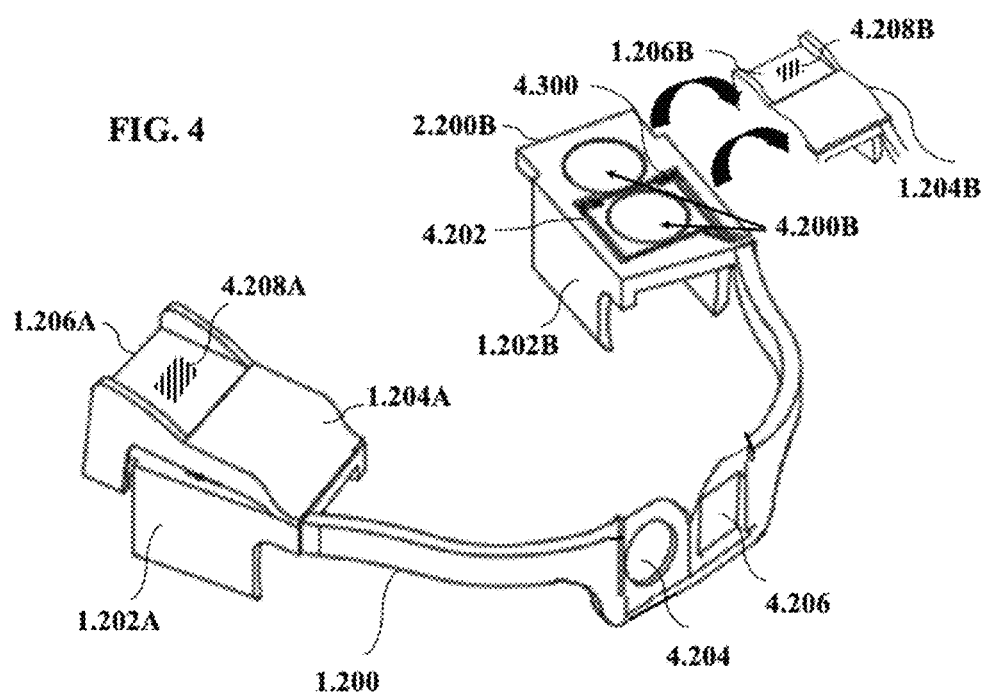
FIG. 4 is a top-angled depiction of an exemplary embodiment of the dental guard with some interior components (magnets).

Referring now to FIG. 4, figuratively peeling back the cover for illustrative purposes exposes two disc magnets 4.200B in the bottom-right magnet housing 2.200B. This same exposed view shows a magnetic field sensor or solenoid 4.202 and button or contact switch 4.300 that tracks teeth-grinding. Because the solenoid and button both take inputs, both are considered sensors. The two sensors may be located right-side-, bottom-only as only one set is needed. However, another embodiment may include a second set of sensors on the left side that might expand the dataset. A coin cell battery 4.204 interconnected with the Bluetooth System on Chip (SoC) 4.206 wirelessly transmits the dental guard data to the cloud server or directly to the user's smartphone app.

Figure 5C:
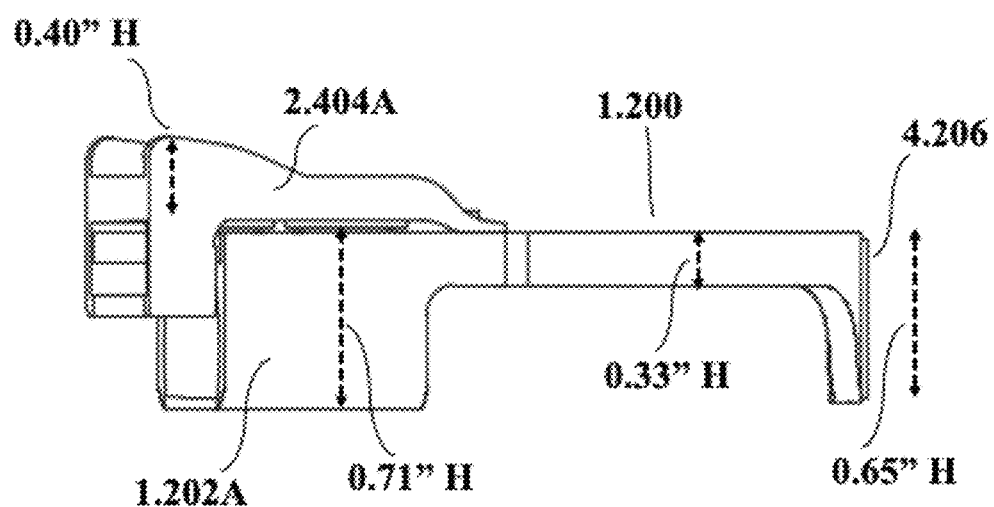
FIG. 5 (A, B, and C) is an overview of key dimensions of an exemplary embodiment of the dental guard.

FIGS. 5A, B, and C contain exemplary dimensions, including overall length of 2.5-2.7 in. and width of 1.7-2.12 in.; strap height of 0.33 in.; left- and right-side, upper-bite tracks' width, 0.59 in.; left- and right-side upper-magnet housings' width, 0.63 in.; frenum gap width, 0.50 in.; lower left- and right-side battery housing height, 0.15 in.; the left- and right-side hook-and-latch safeguard's hook height, 0.06 in.; and the left- and right-side retention walls' height, 0.71 in. The dimensions may vary in this and other embodiments without departing from the scope of the disclosed subject matter.

Figure 6:
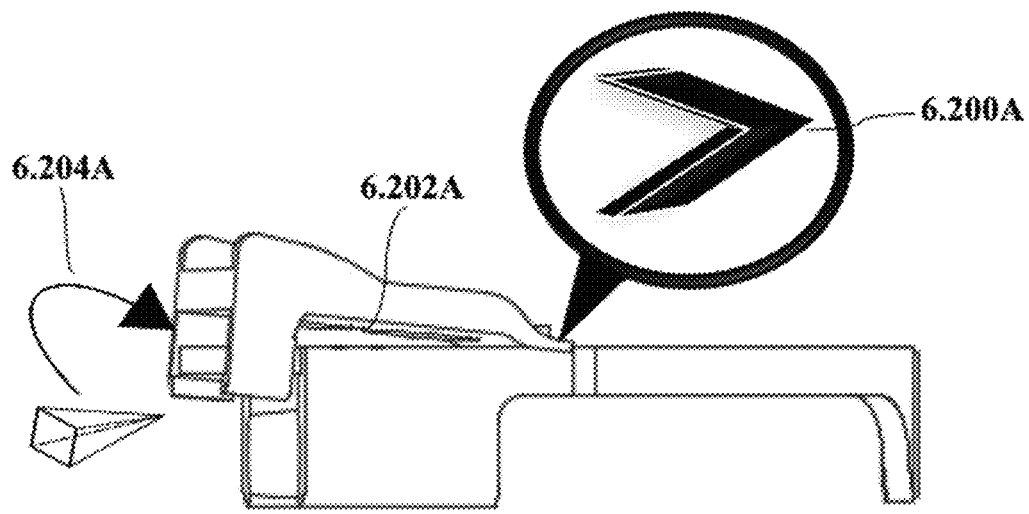
FIG. 6 is a left-side depiction of an exemplary embodiment of the dental guard with a close-up or inlet view of a hinged design feature.

Referring now to FIG. 6 an enlarged view of the hinged holster as a single piece of plastic 6.200A, with no fasteners or exposed internal operational components. This design eliminates the risk of exposed parts breaking off and being swallowed during sleep. Exemplary embodiments may be manufactured from several thermoplastic parts combined into a single piece, using heat fusion, during the injection-molding process.

Figure 7:
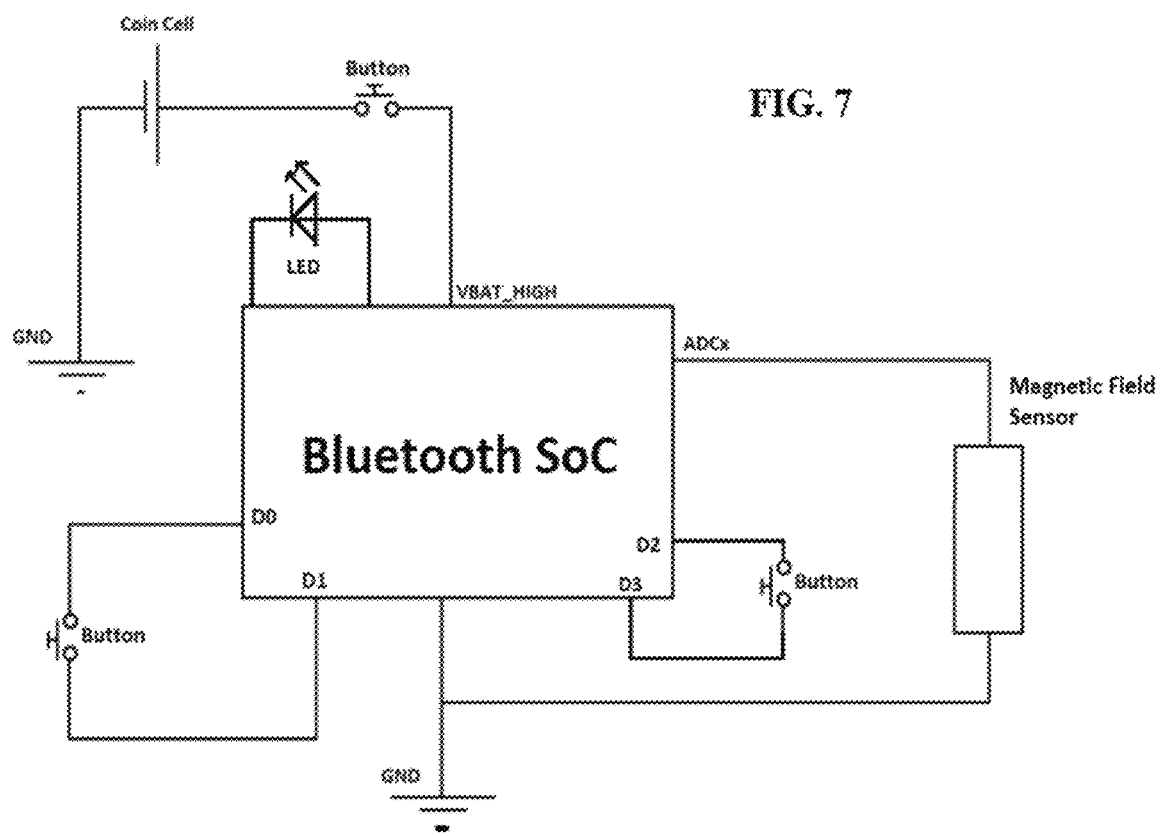
FIG. 7 is an electrical schematic of an exemplary embodiment of the dental guard's Bluetooth system for communicating with an optional mobile app.

Referring now to FIG. 7, an electrical circuit schematic, including a Bluetooth SoC similar to, but not limited to, model DA14531, magnetic field sensor with solenoid (coil of wire with inductive qualities), a contact switch, and coin cell battery, similar to model CR2032, with grounding wires. The SoC's VBAT pin connects with the positive terminal of the coin cell battery voltage, while its ADCx (Analog-to-Digital Converter) pin takes input from the magnetic field sensor, and the button or contact switch connects the D0 and D1 pins of the chip. The magnetic field sensor has an analog interface, but in another embodiment a digital interface can be used instead.

In this configuration, voltage is induced in the solenoid when the opposing magnets move closer to or away from each other with corresponding jaw movement. The movement acts as an input to the ADCx pin on the chip's microcontroller. The button acts as a gateway between the microcontroller's two digital pins. One pin (D0) acts as digital output with a constant voltage and the second (D1), as digital input polling for an expected voltage.

So, the microcontroller polls the input pins and reads their data. The ADCx pin measures the voltage induced in the magnetic field sensor from the movement of the dental guard's magnets and then provides a digital value for further processing.

The digital input pin detects contact between the upper and lower magnets. When the buffer fully closes, the button fully depresses correspondingly and passes the output from D0 to D1. The input pin detects this change and the microcontroller registers both arches as closed. To save power, this sampling may be done at intervals ranging from every 5 to 120 seconds. The button provides significant information about the grinding force exceeding the buffer limit.

As for the SoC's data processing, there are several options in accordance with various embodiments. Since the voltage induced in the magnetic field sensor is directly proportional to the rate of change of magnetic flux in the solenoid, the rate of change in flux is directly related to the rate of change in distance between the magnets. So, if the magnets move at a faster rate (the top and bottom teeth close/open faster), the voltage induced will be greater and the measurement a correspondingly higher digital value. This jaw movement can be analyzed to detect the frequency of jaw-buffer contacts during sleep. The digital pin input can be used to count the number of times the dental guard user bites down using a force beyond the cumulative buffer resistance of the magnets. So, this process allows the magnetic field sensor to provide data regarding the frequency as well as intensity of teeth-grinding.

The Bluetooth SoC facilitates the output channel. Microcontroller analytics are wirelessly and periodically transferred to the smartphone's mobile app and from there to the cloud server. The cloud server and/or app optionally may perform further analytics of the transferred data. The coin cell battery, a 3-volt, lithium variety, is the circuit's power source. Its positive and negative terminals connect to the Bluetooth SoC's voltage and ground pins, respectively. The battery may be disposable along with the dental guard. In an alternative embodiment, a wireless rechargeable battery could be used and powered by an inductive charger or other types of charging arrangement.

In an exemplary embodiment, during periodic or even continuous data monitoring, an alert or alarm function may be added to the smartphone app to notify the user that his or her teeth-grinding has reached or surpassed a certain threshold. The alarm/alert function can be switched, in app settings, to either immediately awaken the user or to indicate a red flag for user review later.

In another embodiment, light-emitting diodes (LEDs), located near the retention band's frenum gap, indicate whether the sensors and Bluetooth are activated. A second button, shown in FIG. 7, activates/deactivates sensors and Bluetooth functionality.

In yet another embodiment, a force-sensing resistor (FSR), similar to model Interlink 402 (https://bit.ly/3cTJGc), may be used—in place of the solenoid/magnetic field system mentioned above—to measure teeth-grinding bite force. The circular Interlink 402 model has a ½-in.-diameter active area, is 0.02-in. thick, and 2.129-in. long. It has two layers separated by a spacer. FSRs basically are a resistor that changes its resistive value depending on how much it is pressed. Use of an FSR is an example of one solution for sensing within the dental guard. This device generally will add layers to the dental guard, but may be one solution for sensing force within.

Figure 8:
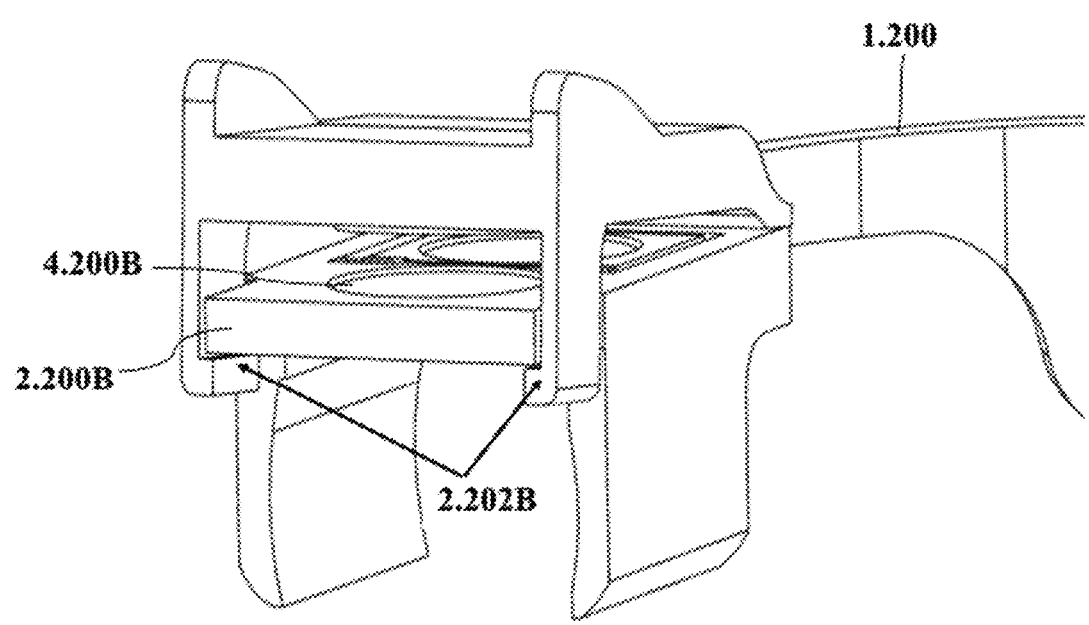
FIG. 8 is a rear-angled view of the exemplary right-side holster.

FIG. 8 depicts the right-side holster containing upper- and lower-magnet housings—the bottom one 2.200B is shown—and the hook-and-latch safeguard with notches protruding from the top-magnet housing extensions to cradle the bottom magnet housing and prevent both housings from opening beyond 2 cm.

Figure 9:
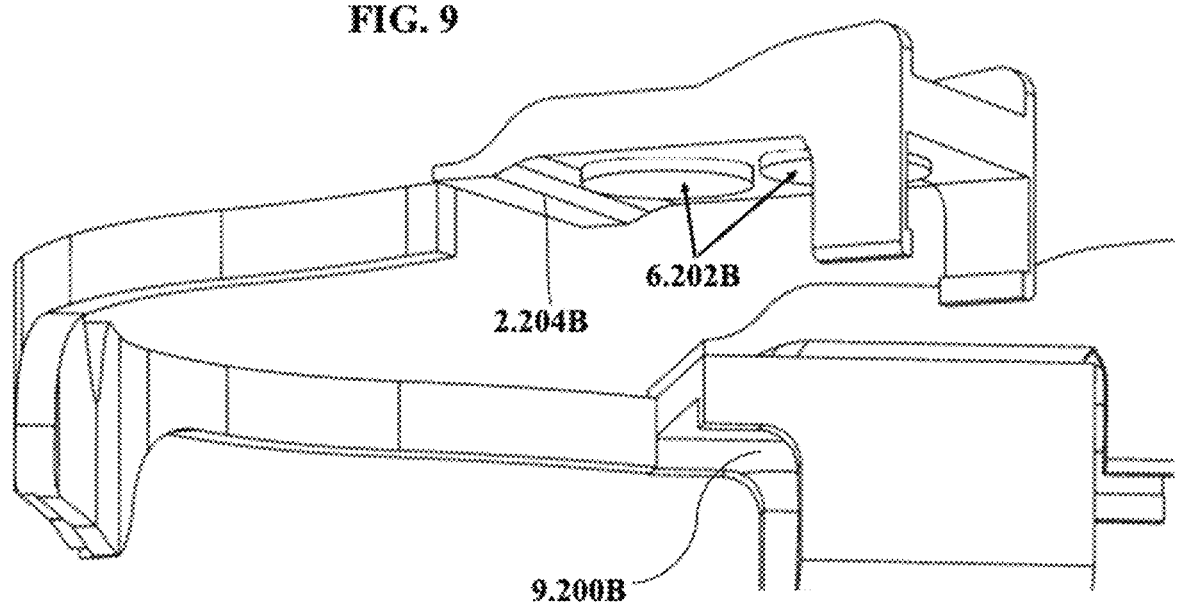
FIG. 9 is a side-angled depiction of some interior and exterior elements of the exemplary dental guard.

FIG. 9 shows two magnets 6.202B in the right-side magnet housing 2.204B.

Figure 10:
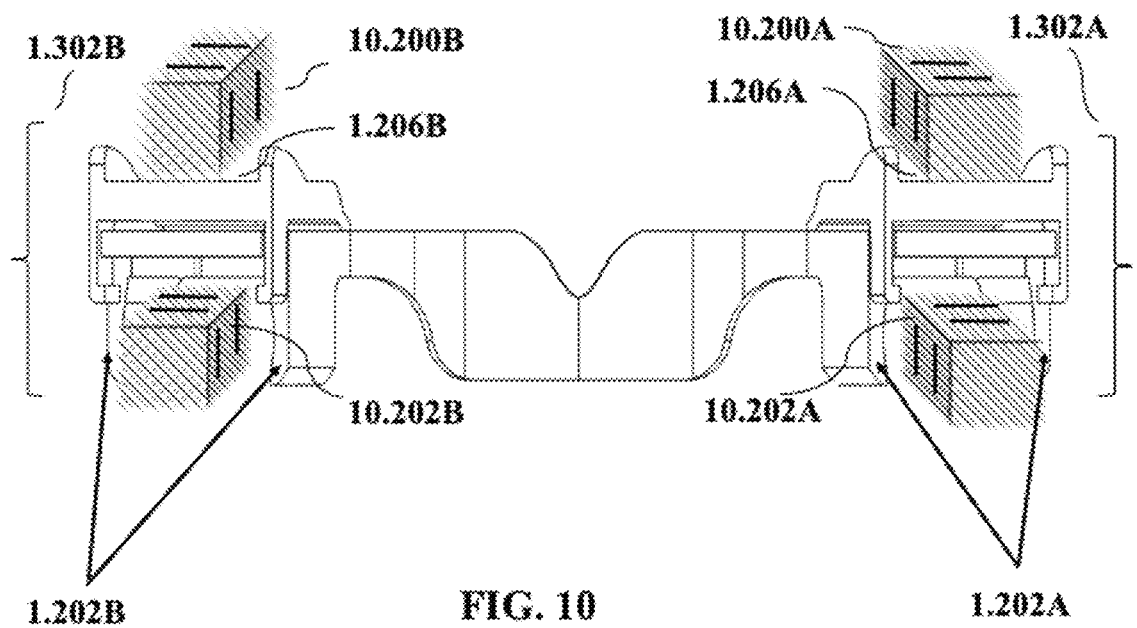
FIG. 10 is a rear-view depiction of human top and bottom arches fitted into the elements of the exemplary rear dental guard.

FIG. 10 shows both holsters containing representations of top teeth 10.200A/10.200B and bottom teeth 10.202A/10.202B in their holsters 1.302A and 1.302B.

Figure 11A:
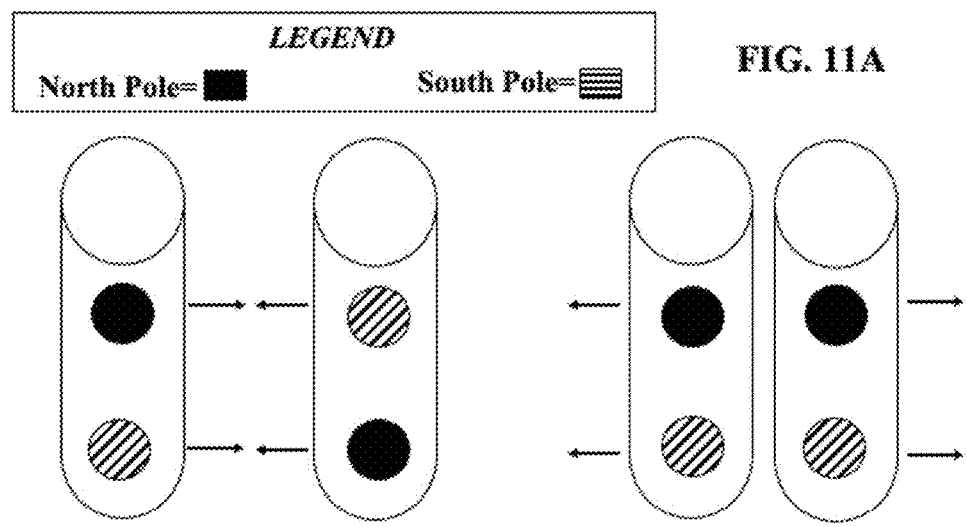
FIG. 11 (A and B) is an overview of reverse magnetism, as used in the exemplary dental guard.
Figure 11B:
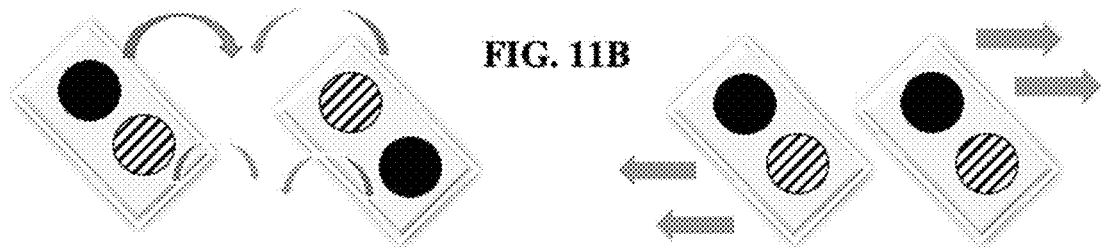

FIGS. 11A and 11B provide an overview of magnetism and reverse magnetism. Magnets have North and South poles. Lines of flux travel from the North to South pole to create a magnetic field. When the North pole of one magnet aligns with the South pole of a second magnet, they attract each other. But when two North poles align with two South poles, the two magnets repel each other.

Exemplary embodiments may use any of a variety of permanent magnets, sizes, and shapes, from wafer-thin, bendable square or rectangular magnets to disc-shaped ones. Magnet strength is permanent under normal conditions with little or no degradation over time. However, magnet strength obeys an inverse square law for distance. In other words, the force is inversely proportional to the distance squared. So, if the distance between two magnets is doubled, then the magnetic force between them falls to a quarter of the initial value, and if distance is halved, then the magnetic force between them increases to four times the initial value.

The maximum magnetic repulsion in PSI is the pressure required to bring the present invention's opposing magnets into complete contact. For consistency, PSI also is used to measure teeth-grinding.

Since the molars fit within their holsters, we may assume the total area of contact between the molars is equal to the area of the left- and right-upper-bite plates, or 0.63" Width× 1.2" Length=0.756 square (sq) in.×2 bite plates=1.512 sq in.

In one embodiment using axially-magnetized D82-N52 magnets, each with a 0.5-in. diameter and 0.125-in. thickness, the maximum magnetic repulsive force produced by one opposing set (two magnets total) is given at 7.17 lbs. (https://bit.ly/3pNqbfT). This maximum value is the result of the magnets coming in complete contact.

Figure 16:
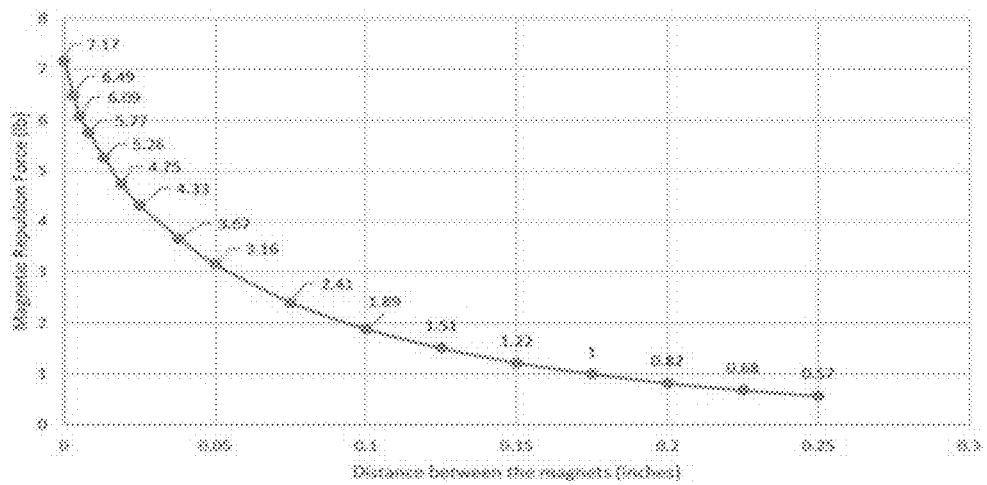
FIG. 16 is a chart showing the distance between the to D82-N52 magnets along their axis and the relationship between the resulting magnetic repulsion force.

The chart in FIG. 16 shows the distance between the two D82-N52 magnets along their axis and the relationship between the resulting magnetic repulsion force.

Figure 17:
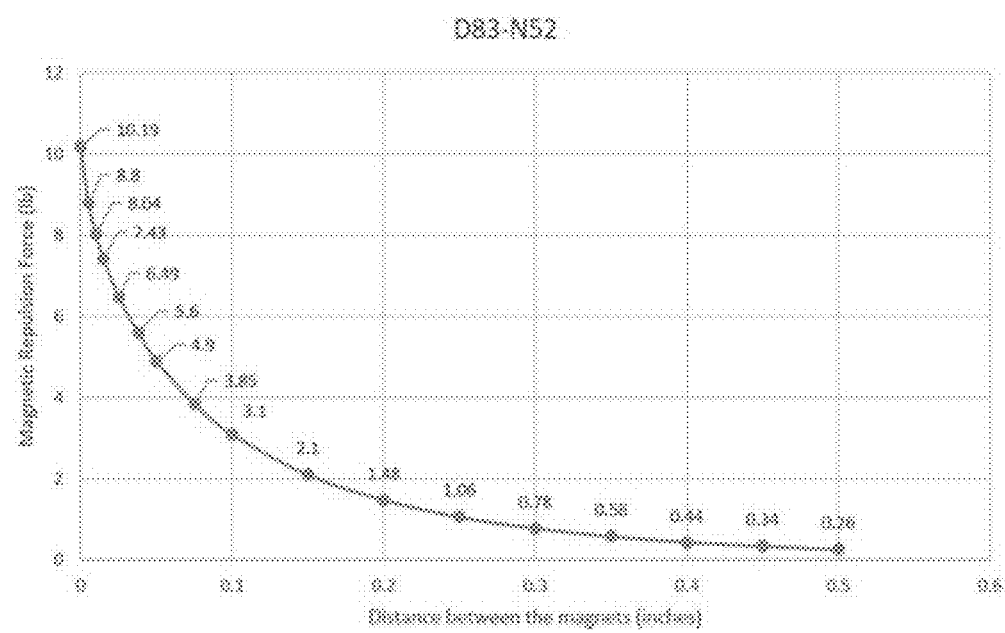
FIG. 17 is a chart showing the distance between two D83-N52 magnets along their axis and the relationship to the resulting magnetic repulsion force.

The chart in FIG. 17 shows the distance between two D83-N52 magnets along their axis and the relationship to the resulting magnetic repulsion force.

So, for the two sets of opposing magnets (four magnets total) on one side of the dental guard, the maximum magnetic repulsive force is approximately 14.34 lbs. or 7.17 lbs.× 2=14.34 lbs., and the total maximum magnetic repulsive force generated by all four sets of D82-N52 magnets is approximately 28.68 lbs.

The pressure produced by such maximum magnetic repulsion between the top and bottom molars is given by the formula:

Pressure=max. total magnetic force/total area of contact between the molar teeth, or Pressure=28.68/ 1.512 sq in.=18.968 PSI.

Thicker magnets with the same diameter could be substituted to increase magnetic force. For instance, the maximum magnetic repulsive force of one set of D83-N52 magnets, with 0.5-in. diameter and 0.1875-in. thickness, is given at 10.19 lbs.

So, using four sets of D83-N52 magnets, the total maximum magnetic repulsive force achieved by the present invention is approximately 40.76 lbs., and the resulting pressure produced by this magnetic repulsion between the top and bottom molars is 40.76/1.512 sq in.=26.957 PSI or:

2.99 percent of the upper-range bite force, 900 PSI, applied amid teeth grinding;

a stronger 17.97 percent of the 150 PSI applied when deliberately clenching teeth; and a still-stronger 39.64 percent of normal chewing's 68 PSI.

This magnetic pressure works against the bite pressure exerted on the molars. To accommodate this dynamic, a magnetic buffer 6.204A, as depicted in FIG. 6, may be deployed in each holster's chamber between the top and bottom arches. Buffer size must be wide and strong enough to prevent teeth from grinding, yet still narrow enough to prevent discomfort.

Roughly the shape of a prism, the magnetic buffer volume becomes zero when equaled or exceeded by the bite force, but when no bite force is applied the buffer volume remains constant because of the 2-cm stopgap limitation built into each holster.

Figure 18:
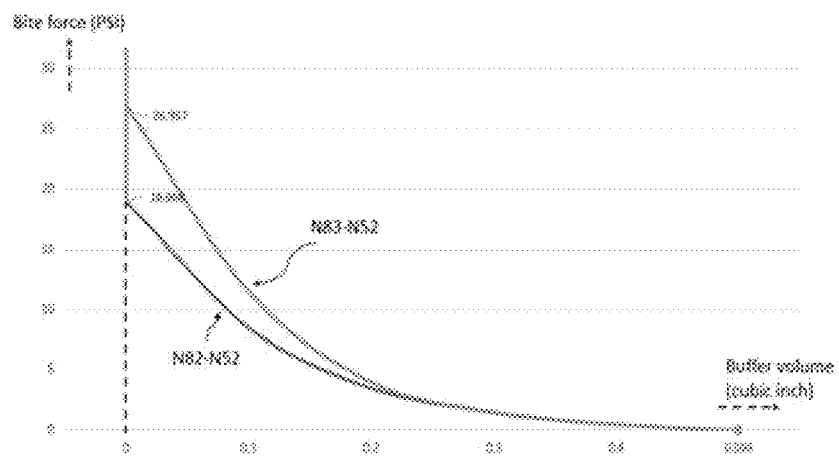
FIG. 18 is a chart showing how the buffer volume remains constant at 0.594 cubic in. for both types of magnet configurations when no bite pressure is applied.

The chart sin FIG. 18 hows how the buffer volume remains constant at 0.594 cubic in. for both types of magnet configurations when no bite pressure is applied. When the bite pressure equals or exceeds the magnetic repulsion pressure for both magnet types shown, the buffer volume becomes zero. When the bite force is less than the maximum repulsion force between the magnets, the relation between the bite force and buffer volume follows the inverse square relation.

In the chart shown in FIG. 18, the lines are curved because magnetic repulsion obeys the inverse square relation with the distance between the magnets. Also, the distance between the magnets relates to the buffer height within the present invention.

Since, the magnetic repulsive force is inversely proportional to the square of the distance between the magnets:

Repulsion Force$\propto$1/(Distance between magnets)$^2$

Dividing both sides by the square of the contact area (Area$^2$) of the molars

Repulsion Force/(Area)$^2$$\propto$1/(Distance between magnets×Area)$^2$

Repulsion Force/Area$\propto$Area/(Distance between magnets×Area)$^2$

Since magnetic repulsion force's pressure, in PSI, is equal to the magnetic repulsion force per unit of molar contact area, and that area is constant during a bite, we can deduce the fourth expression above as:

Repulsion PSI$\propto$1/(Distance between magnets×Area)$^2$

Since the total buffer volume is given by multiplying the area of the molar contacts with the height of the buffer, and buffer height relates to the distance between the magnets:

Repulsion PSI$\propto$1/(Total buffer volume)$^2$

To reiterate, the magnetic repulsion's pressure is inversely proportional to the square of buffer volume. So, when the bite PSI is within the PSI of magnetic repulsion, the buffer volume is determined by the magnetic repulsion. Therefore, the graph within the maximum PSI of magnetic repulsion is a curved line.

Per the chart shown in FIG. 18, once the bite PSI exceeds the maximum PSI of magnetic repulsion (26.957 for N83-N52 and 18.968 for N82-N52), the lines flow vertically upwards by disregarding the relation calculated above and the buffer volume remains zero.

Magnetic buffer length and volume ultimately are approximations, due to magnetism's mercurial or fluctuating properties, intended to provide a general scope of the present invention's bruxism-fighting efficiency.

While the configurations disclosed may not eliminate the heaviest teeth-grinding, they do reduce or minimize teeth-grinding's impact, especially when their reverse-magnetic buffer works in tandem with the dual holster design. Further, through a repetitive process not unlike muscle memory, the bite force resistance and reverse magnetic field's give or malleability may, over time, help train jaws and teeth not to grind or to grind less during sleep. And it is possible, through various embodiments, to increase the buffer strength.

In one embodiment, reverse magnetic buffer strength may be increased, at least minimally, by adding a second solenoid with a ferromagnetic (iron) core that would convert both solenoids to electromagnets. An electromagnet is a type of commonly-classed non-permanent magnet in which the magnetic field is produced by an electric current. Electromagnets usually consist of wire wound into a coil. A current through the wire creates a magnetic field which is concentrated in the hole, denoting the coil's center. This embodiment likely would require a larger battery capacity.

In another embodiment, because portions of the left- and right-side opposing magnetic fields flow outward and away from the dental guard, the interior-upper 1.204A/1.204B and interior-lower 2.200A/2.200B magnet housings, specifically, are coated with magnetic tape or film to deflect or re-route the wayward magnetic fields back towards their opposite magnets. Known as magnetic shielding, this process works by redirecting the magnetic field, that is, giving it a path of least resistance to follow. So, it may be possible, through careful placement of the magnetic tape, to further increase the present invention's strength, adding a few PSI to its reverse magnetic buffer. One generic example of magnetic shielding film on the market is a model made from an amorphous cobalt alloy for shielding of low-frequency alternating magnetic fields.

An alternative embodiment uses diamagnets to further increase repulsive magnetic force. Diamagnetism is a repulsive property that arises from Lenz's law, which holds: Creating a magnetic field will move electrons; moving electrons also creates a magnetic field; and the newly-created magnetic field will oppose the original one. Diamagnetic metals include copper, gold, and zinc. All materials have diamagnetism, but other forms of magnetism are stronger, so materials that also have other kinds of magnetism are categorized by their strongest type.

Exposing any material to a magnetic field will cause the electrons in each atom to move in a way that creates a tiny magnetic field in the opposite direction. However, this repulsion is so tiny that it requires very specialized equipment to measure, which may be feasible with further development.

In other various embodiments, pinholes in the top bite pads and bottom retention walls 9.200A/9.200B each intermittingly emit brief flashes of far ultraviolet C (far-UVC) light to kill airborne viruses without harming human tissues. Penlights, wired to the coin cell battery, are the source of this low-cost far-UVC light. Broad-spectrum UVC light, which has a wavelength of between 200 to 400 nanometers (nm), long has been considered highly effective at killing bacteria and viruses by destroying the molecular bonds that hold their DNA together.

In an alternative embodiment, related to user comfort, in addition to or in lieu of the far-UVC lights, the top bite plates and lower retention walls intermittingly vibrate to help relax the jaws and user overall. A DC, 3-volt, 12,000 rotations-per-minute (RPM), coin-shaped mini vibration motor, wired to the coin-cell battery, powers the vibrations. The motor is 0.39-in. diameter by 0.12-in. tall. This embodiment likely would require a wirelessly rechargeable battery.

The hygiene and relaxation functions could be controlled in the smartphone app settings. In accordance with various embodiments:

1. User registers for new account in app using mobile device with internet connection;
2. During sleep, solenoid sensor and switch button track teeth-grinding data, specifically grinding intensity and buffer contacts between top and bottom teeth;
3. The data are continuously fed to the user's smartphone or mobile device using the Bluetooth SoC;
4. The smartphone app continuously processes and stores the data and sounds an alarm or another alert when teeth-grinding exceeds a certain level in a certain interval.
5. The stored data are uploaded to the cloud server periodically for back-up purposes and so they can be further analyzed by the user's dentist to aide in diagnostic and treatment options.

Figure 12:
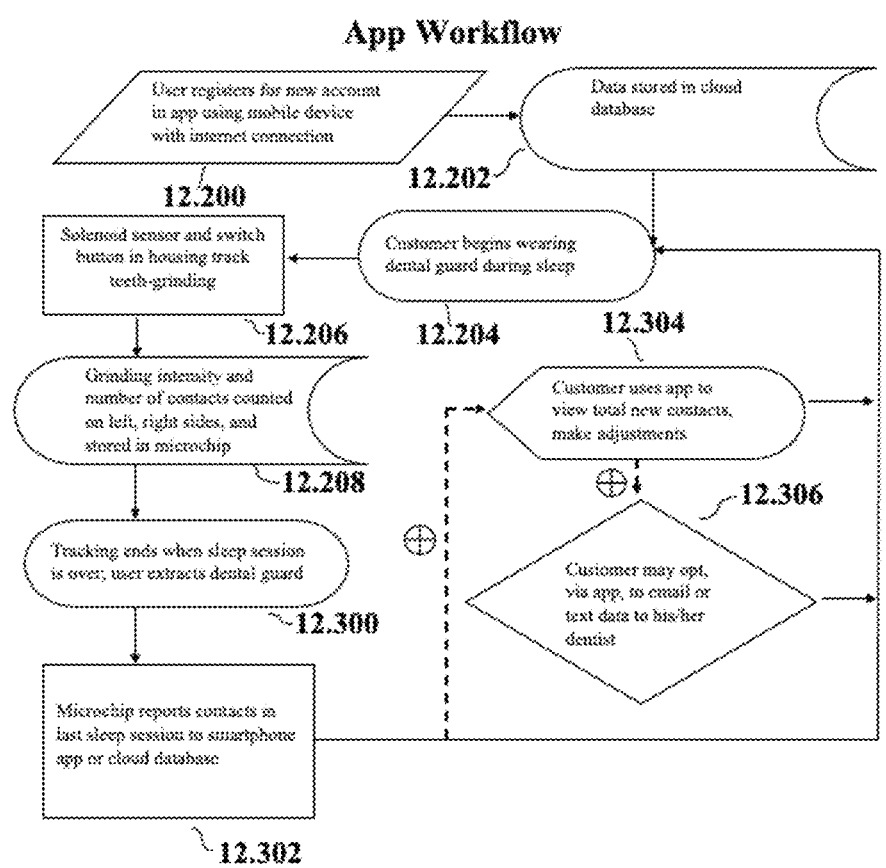
FIG. 12 is an app workflow for providing an exemplary dental guard performance data.

FIG. 12 is a mobile app workflow ranging from 12.200 to 12.306. The dental guard user registers for a new account in the app using a mobile device (process 12.200). When the user begins using (Process 12.204) the dental guard, the sensor tracks opposing magnet contacts (Process 12.206), and an onboard Bluetooth/Wi-Fi microchip then transfers the data (Process 12.302) to a smartphone app cloud database. The account data is stored in cloud servers for back-up and future reference.

The user opens the app to view the total number of top-bottom teeth contacts and grinding intensity (process 12.304), and then adjusts dental guard usage or sleeping habits accordingly. The user may use the app to send data to his or her dentist via texts or emails (Process 12.306).

Figure 13:
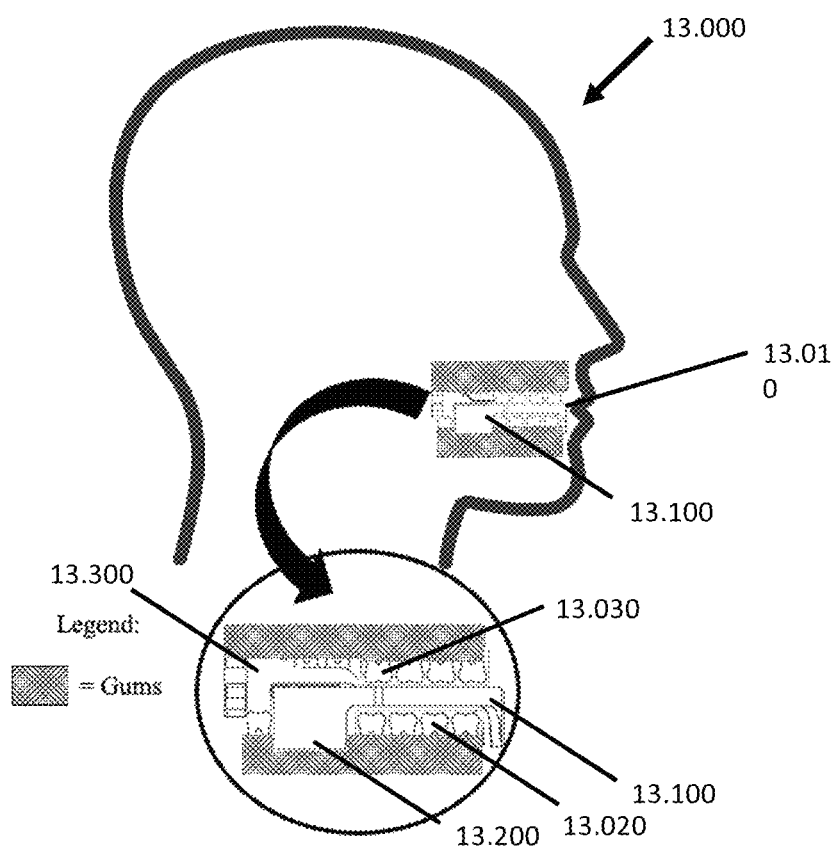
FIG. 13 is an exemplary embodiment of the dental appliance inserted in the mouth of a user.

Referring now to FIG. 13, a user 13.000 is depicted having a dental appliance 13.100 within a mouth cavity 13.010 as if during sleep. Dental appliance 13.100 includes a lower tooth seat 13.200 which is in contact with at least one lower tooth 13.020. Dental appliance 13.100 also includes an upper tooth seat 13.300 which is in contact with at least one upper tooth 13.030. Dental appliance 13.100 is representative of those described previously.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context entails otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While the disclosed subject matter has been described in terms of illustrative embodiments, it will be understood by those skilled in the art that various modifications can be made thereto without departing from the scope of the claimed subject matter as set forth in the claims.

What is claimed is:

1. A dental appliance, comprising:
   a first lower-tooth seat configured to accommodate at least one lower tooth and having a first lower magnet coupled thereto;
   a second lower-tooth seat configured to accommodate at least one second lower tooth and having a second lower magnet coupled thereto;
   a support structure coupling the first lower-tooth seat to the second lower-tooth seat;
   a first upper-tooth seat configured to accommodate at least one upper tooth and having a first upper magnet coupled thereto, the first upper-tooth seat movably coupled by a first hinge to the first lower-tooth seat;
   a second upper-tooth seat configured to accommodate at least one second upper tooth and having a second upper magnet coupled thereto, the second upper-tooth seat movably coupled by a second hinge to the second lower-tooth seat;
   wherein a pole of the first lower magnet substantially faces a matching pole of the first upper magnet; and
   wherein a pole of the second lower magnet substantially faces a matching pole of the second upper magnet.

2. The dental appliance of claim 1, further comprising:
   a first magnetic buffer configured to maintain a minimum spacing between the first upper-tooth seat and the first lower-tooth seat; and
   a second magnetic buffer configured to maintain a minimum spacing between the second upper tooth-seat and the second lower-tooth seat.

3. The dental appliance of claim 1, wherein the first upper and lower magnets include D83-N52 magnets; and
   wherein the second upper and lower magnets include D83-N52 magnets.

4. The dental appliance of claim 1, wherein the first upper and lower magnets include electromagnets; and
   wherein the second upper and lower magnets include electromagnets.

5. The dental appliance of claim 1, further comprising:
   a force-sensing circuit configured to detect force between the first upper- and lower-tooth seats and the second upper- and lower-tooth seats.

6. The dental appliance of claim 5, wherein the force-sensing circuit is configured for wireless communication for sending wireless signals representative of a force being sensed.

7. A method, comprising:
   providing a dental appliance which resists teeth grinding by application of magnetic repulsion, wherein the dental appliance includes:
   a first lower-tooth seat configured to accommodate at least one lower tooth and having a first lower magnet coupled thereto;
   a second lower-tooth seat configured to accommodate at least one second lower tooth and having a second lower magnet coupled thereto;
   a support structure coupling the first lower-tooth seat to the second lower-tooth seat;
   a first upper-tooth seat configured to accommodate at least one upper tooth and having first-upper magnet coupled thereto, the first upper-tooth seat movably coupled by a first hinge to the first lower-tooth seat;
   a second upper-tooth seat configured to accommodate at least one second upper tooth and having a second upper magnet coupled thereto, the second upper-tooth seat movably coupled by a second hinge to the second lower-tooth seat;
   wherein a pole of the first lower magnet substantially faces a matching pole of the first upper magnet;
   wherein a pole of the second lower magnet substantially faces a matching pole of the second upper magnet;
   sensing a repulsive force between the respective upper and lower magnets; and
   sending a signal representative of the repulsive force to a computing device.

8. The dental appliance of claim 1, wherein the support structure is a retention band connecting the first and second lower-tooth seats each.

9. The dental appliance of claim 1, wherein the first and second upper- and lower-tooth seats comprise a first and second holster wall configured to keep the dental appliance in place.

10. The dental appliance of claim 9, wherein the first and second holster walls are substantially parallel.

11. The dental appliance of claim 9, wherein the first and second holster walls are angled downward and inward such that both are configured to fit snugly over respective lower teeth.

12. The dental appliance of claim 9, wherein the first and second holster walls are lined with a material to increase tooth grip.

13. The dental appliance of claim 1, wherein the first and second upper-tooth seats have hook-and-latch safeguards configured to prevent jaw overextensions and corresponding heavy teeth-grinding.

14. The dental appliance of claim 2, wherein the first and second magnetic buffers are a repulsive magnetic field.

15. The dental appliance of claim 14, wherein the maximum spacing is 2 cm.

16. The dental appliance of claim 10, wherein the electromagnets are configured to cause increasing repelling magnetic forces as bite surfaces of the dental appliance come closer together.

17. The dental appliance of claim 5, wherein the force-sensing circuit includes a magnetic field sensor.

18. The dental appliance of claim 5, wherein the force-sensing circuit includes a force-sensing resistor.

19. The dental appliance of claim 6, wherein the wireless communication is configured to communicate with a mobile device.

20. The dental appliance of claim 6, wherein the wireless communication is configured to transmit data regarding a frequency and intensity of teeth-grinding.

* * * * *